United States Patent [19]

Kornfeld et al.

[11] 4,246,265

[45] Jan. 20, 1981

[54] 6-N-PROPYL-8α-METHOXYMETHYL OR METHYLMERCAPTOMETHYLERGOLINES AND RELATED COMPOUNDS

[75] Inventors: Edmund C. Kornfeld; Nicholas J. Bach, both of Indianapolis, Ind.

[73] Assignee: Eli Lilly and Company, Indianapolis, Ind.

[21] Appl. No.: 80,768

[22] Filed: Oct. 1, 1979

[51] Int. Cl.³ .......................................... A61V 31/48
[52] U.S. Cl. ................................................. 424/261
[58] Field of Search ..................................... 424/261

[56] References Cited

U.S. PATENT DOCUMENTS

| | | | |
|---|---|---|---|
| 3,901,894 | 8/1975 | Kornfeld et al. | 424/261 |
| 4,166,182 | 8/1979 | Kornfeld et al. | 424/261 |

OTHER PUBLICATIONS

Stutz et al., J. Med. Chem., 21, 754 (1978).

Primary Examiner—Stanley J. Friedman
Attorney, Agent, or Firm—James L. Rowe; Arthur R. Whale

[57] ABSTRACT

D-6-n-propyl-8α-methoxymethyl or methylmercaptomethylergoline, dopaminergic drugs are used to treat Parkinsonism and to inhibit prolactin secretion.

4 Claims, No Drawings

6-N-PROPYL-8α-METHOXYMETHYL OR METHYLMERCAPTOMETHYLERGOLINES AND RELATED COMPOUNDS

BACKGROUND OF THE INVENTION

Compounds based on the ergoline ring system:

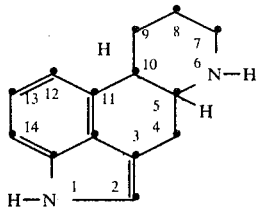

have a suprising variety of pharmaceutical activities. For example, many of the amides of lysergic acid, which is 8β-carboxy-6-methyl-9-ergolene, have valuable and unique pharmacologic properties. The trivial name "ergoline" is given to the above structure and the 9,10 double bonded compound—related to lysergic acid— is called a 9-ergolene rather than a 9,10-didehydro-ergoline. The name D-ergoline or D-8-ergolene or D-9-ergolene is used herein in naming specific compounds. The letter "D" indicates that the C-5 carbon atom configuration has the absolute stereochemistry designated as R and that the hydrogen is β—above the plane of the ring system. However, modern usage has tended to omit the "D", on the ground that the newly synthesized ergolines or ergolenes are universally derivatives of natural products such as lysergic acid or elymoclavine, both of which have R stereochemical— "D" series—configuration and in which the stereochemical integrity at C-5 is maintained during various synthetic procedures. It should be understood that all of the compounds and the classes of ergolines or ergolenes disclosed herein also have the R stereochemical configuration, whether or not the specific or generic name is preceded by a "D".

Among the pharmacologically active amides of lysergic acid are included naturally-occurring oxytoxic alkaloids—ergocornine, ergokryptine, ergonovine, ergocristine, ergosine, ergotamine, etc.—and synthetic oxytocics such as methergine as well as the synthetic hallucinogen lysergic acid diethylamide or LSD. The amides of 6-methyl-8-carboxyergoline, known generically as dihydroergot alkaloids, are oxytocic agents of lower potency and also lower toxicity than the ergot alkaloids themselves.

Recently, it has been found by Clemens, Semonsky, Meites, and their various co-workers that many ergot-related drugs have activity as prolactin inhibitors. Ergocornine, dihydroergocornine, 2-bromo-α-ergokryptine and D-6-methyl-8-cyanomethylergoline (Semonsky et al U.S. Pat. No. 3,732,231) are examples of such drugs. References embodying some of the newer findings in the field of ergoline and ergolene chemistry include the following: Nagasawa and Meites, *Proc. Soc. Exp't'l. Biol. Med.*, 135, 469 (1970); Lutterbeck et al., *Brit. Med. J.*, 228, (July 24, 1971); Heuson et al., *Europ. J. Cancer*, 353 (1970); *Coll. Czech. Chem. Commun.*, 33, 577 (1968); *Nature*, 221, 666 (1969); Seda et al., *J. Reprod. Fert.*, 24, 263 (1971); Mantle and Finn, id, 441; Semonsky and co-workers, *Coll. Czech. Chem. Comm.*, 36, 2200 (1971); Schaar and Clemens, *Endocr.*, 90, 285–8 (1972); Clemens and Schaar, *Proc. Soc. Exp. Biol. Med.*, 139, 659–662 (1972), Bach and Kornfeld, *Tetrahedron Letters*, 3225 (1974) and Sweeney, Clemens, Kornfeld and Poore, 64th Annual Meeting, American Association for Cancer Research, April 1973. Recently issued patents in the field of the ergolines or of lysergic acid derivatives include the following: U.S. Pat. No. 3,923,812, U.S. Pat. No. 3,929,796, U.S. Pat. No. 3,944,582, U.S. Pat. No. 3,934,772, U.S. Pat. No. 3,954,988, U.S. Pat. No. 3,957,785, U.S. Pat. No. 3,966,739, U.S. Pat. No. 3,968,111, U.S. Pat. No. 4,001,242. Many other related and older patents can be found in Patent Office Classification Files 260-256.4 and 260-285.5.

U.S. Pat. No. 4,166,182 issued Aug. 28, 1979 (filed February 8, 1978) discloses and claims D-6-n-propyl-8β-methoxymethylergoline and D-6-n-propyl-8β-methylmercaptomethylergoline, among other compounds. The latter drug has been given the generic name pergolide and is presently undergoing a clinical trial as a prolactin inhibitor and in the treatment of Parkinsonism.

Stutz et al *J. Med. Chem.*, 21, 754 (1978) describes the preparation of a group of 6-methyl-8α-arylthiomethylergolines which were found to be dopaminergic agents with a potential in the treatment of Parkinson's syndrome. The 8α-isomer of the Semonsky et al compound, 6-methyl-8β-cyanomethylergoline, was also prepared and "--- was rather unexpectedly found to be a highly active dopaminergic stimulant in the Ungerstedt test ---.". 6-Methyl-8β-methylthiomethyl ergolines are disclosed and claimed in U.S. Pat. Nos. 3,959,288 and 3,901,894 respectively as prolactin inhibitors.

Parkinson's disease, also known as paralysis agitans or shaking palsy, was first described in the late 18th century. It is characterized by tremor, muscular rigidity and loss of postural reflexes. The disease usually progresses slowly with intervals of 10 to 20 years elapsing before the symptoms cause incapacity. The terms "Parkinsonism" and "the Parkinsonian syndrome" include not only Parkinson's disease but also drug-induced Parkinsonism and post-encephalitic Parkinsonism. Treatment of Parkinsonism involves symptomatic, supportive and palliative therapy. Parkinson's disease has been treated with various anticholinergic agents, which agents have a greater beneficial effect on rigidity and akinesia than on tremor. More recently l-dopa (1-dihydroxyphenylalanine) has been used because of the finding that there is an altered catecholamine content in the brains of patients afflicted with Parkinsonism. Unfortunately, l-dopa is rapidly metabolized. It has been suggested, therefore, that monoamineoxidase inhibitors be used to retard the degradation of cerebral catechol amines. The use of l-dopa with a decarboxylase inhibitor was also designed to increase the level of l-dopa in the brain and hopefully thereby to alleviate the symptoms of Parkinsonism. It has also been suggested (by Corrodi and coworkers) that certain ergot derivatives, such as the naturally occurring alkaloid, ergocornine, are direct dopamine receptor stimulants of long duration and may therefore prove to be of value in the treatment of Parkinson's disease [see *J. Pharm. Pharmac.*, 25, 409 (1973)]. Johnson et al. in *Experientia*, 29, 763 (1973) discuss the evidence of Corrodi et al. that ergocornine and 2-bromo-α-ergokryptine simulate dopamine receptors and extended their observations to other ergot alkaloids (see also *Brit. J. Pharm.*, 56, 59 (1976). Trever W. Stone writing in *Brain Research*, 72, 1977 (1974)

verified the above experiments and produced further evidence that ergot alkaloids have a dopamine receptor stimulating action.

Description of the Invention

This invention provides a group of extremely potent prolactin inhibitors and drugs for treating Parkinsonism belonging to the ergoline series and having the following structure:

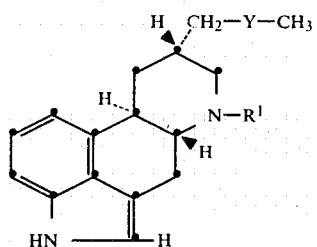

wherein Y is O or S and R$^1$ is n-propyl, and pharmaceutically-acceptable acid addition salts thereof.

The pharmaceutically-acceptable acid addition salts of this invention include salts derived from inorganic acids such as: hydrochloric acid, nitric acid, phosphoric acid, sulfuric acid, hydrobromic acid, hydriodic acid, nitrous acid, phosphorus acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

The compounds of this invention are prepared as follows: Lysergic Acid, D-6-methyl-8β-carboxy-9-ergolene, is hydrogenated over a noble metal catalyst such as a platinum catalyst to yield the corresponding D-6-methyl-8β-carboxyergoline. Esterification with acidic methanol yields the corresponding 8β-methoxycarbonyl derivative. This compound is next N-demethylated by treatment with cyanogen bromide (which displaces the methyl with CN) followed by reduction of the resulting 6-cyano derivative with zinc and acetic acid. 8β-Methoxycarbonylergoline is next alkylated at the 6-position with propyl iodide to yield the corresponding D-6-n-propyl-8β-methoxycarbonylergoline.

D-6-n-propyl-8β-methoxycarbonylergoline thus prepared is next reacted with m-chloroperbenzoic acid and the resulting intermediate treated with a mixture of acetic anhydride and triethylamine, thus forming D-6-n-propyl-8-methoxycarbonyl-7-ergolene. The procedure is patterned after that of Stutz and Stadler, *Tetrahedron Lett.*, 5095 (1973) who carried out a similar reaction on the corresponding D-6-methyl derivative. Reduction of the 7,8-double bond with hydrogen in the presence of a heavy metal catalyst, such as a platinum catalyst, yields the corresponding D-6-n-propyl-8α-methoxycarbonylergoline. This reduction procedure is described in Stutz et al. *J. Med. Chem.*, 21, 754 (1978). Continuing to follow this latter Stutz et al. procedure, the methoxycarbonyl group is reduced to an hydroxymethyl group with lithium aluminumhydride. The hydroxymethyl group is then esterified with methane sulfonylchloride and the resulting mesylate reacted with the sodium salt of methyl mercaptan or sodium methylate as taught in U.S. Pat. Nos. 4,166,182; 3,959,288; or 3,901,894. The 8α-methoxymethyl or 8α-methylmercaptomethyl derivatives thus produced are customarily isolated in the form of an acid addition salt thereof such as a salt with methane sulfonic acid or with maleic acid or the like.

This invention is further illustrated by the following specific examples.

EXAMPLE 1

Preparation of D-6-n-propyl-8β-methoxycarbonylergoline 10 g. of D-6-methyl-8β-methoxycarbonylergoline (methyl dihydrolysergate) were dissolved in 300 ml. of methylene dichloride. 10 g. of cyanogen bromide were added and the resulting mixture stirred overnight at room temperature. The organic layer was washed first with dilute aqueous hydrochloric acid to remove any unreacted starting material and then with water. The organic layer was dried and the solvent removed therefrom by evaporation. 10 g. of D-6-cyano-8β-methoxycarbonylergoline melting at 205°-6° C. were obtained.

A mixture of 10 g. of the above 6-cyanoergoline, 50 g. of zinc dust, 400 ml. of glacial acetic acid and 80 ml. of water was heated to reflux temperature under a nitrogen atmosphere for 16.5 hours. The reaction mixture was then filtered and the filtrate poured over ice. The diluted filtrate was made basic by the addition of 14 N aqueous ammonium hydroxide. The now alkaline filtrate was extracted several times with chloroform, the chloroform extracts combined and the combined extracts washed with saturated aqueous sodium chloride and then dried. Evaporation of the chloroform yielded D-8β-methoxycarbonylergoline.

This product without further purification was dissolved in 250 ml. of dimethylformamide (DMF). 7 g. of potassium carbonate were added followed by 8.8 ml. of n-propyliodide. The reaction mixture was stirred at room temperature for about 21 hours after which time it was diluted with water. The diluted reaction mixture was extracted several times with ethyl acetate. The ethyl acetate extracts were combined and the combined extracts washed with saturated aqueous sodium chloride and then dried. Evaporation of the solvent yielded D-6-n-propyl-8β-methoxycarbonylergoline as a crystalline residue. The crystals were washed with a mixture of ether and hexane. D-6-n-propyl-8β-methoxycarbonylergoline thus obtained melted at about 206°-208° C.; yield=5.6 g.

EXAMPLE 2

Preparation of D-6-n-propyl-8-methoxycarbonyl-7-ergolene

Three grams of D-6-n-propyl-8β-methoxycarbonylergoline were dissolved in 150 ml. of methylene dichloride and the solution cooled to a temperature in the range of −25° to −35° C. A solution of 2 g. of m-chloroperbenzoic acid in 15 ml. of methylenedichloride was added thereto in dropwise fashion. The reaction mixture was stirred in the same temperature range for about 20 minutes, after which time 1.0 ml. of acetic anhydride and 6.9 ml. of triethylamine were added. This subsequent reaction mixture was stirred for 90 minutes at a temperature in the range of −30° to +5° C. The reaction mixture was then diluted with aqueous sodium bicarbonate and the resulting mixture extracted with methylene dichloride. The methylene dichloride extract was washed with saturated aqueous sodium chloride and then dried. Evaporation of the solvent yielded a residue containing D-6-n-propyl-8-methoxycarbonyl-7-ergolene prepared as above. A chloroform solution of the residue was chromatographed over 150 g. of florisil using chloroform containing 0–1 percent methanol as the eluant. Fractions shown by TLC to contain D-6-n-propyl-8-methoxycarbonyl-7-ergolene were combined and the solvent evaporated therefrom. About 700 mg. were obtained melting at about 193°–194° C. with decomposition.

Analysis Calculated: C, 73.52; H, 7.14; N, 9.03; Found: C, 73.58; H, 6.85; N, 8.93.

EXAMPLE 3

Preparation of
D-6-n-propyl-8α-methoxycarbonylergoline

About 420 mg. of D-6-n-propyl-8-methoxycarbonyl-7-ergolene were dissolved in 50 ml. of a 1:2 DMF/glacial acetic acid solvent mixture. The solution was hydrogenated in an Adams machine at a hydrogen pressure of about 60 psi over 0.5 g. of a platinum oxide catalyst. After the theoretical amount of hydrogen had been absorbed, the hydrogenation mixture was filtered and the filtrate poured over ice. The aqueous mixture was made basic with 14 N aqueous ammonium hydroxide. The resulting alkaline mixture was extracted with ethyl acetate. The ethyl acetate extract was washed with water and with saturated aqueous sodium chloride and then dried. Evaporation of the ethyl acetate yielded a residue which contained two major spots on TLC, indicating 2 reaction products, the 8α and 8β isomers. An ether solution of the residue was chromatographed over 30 g. of florisil using ether as the eluant. The first eluate fraction was shown to contain two major spots by TLC but fractions 2–6 contained only single spot material. The first fraction was subjected to preparative thin-layer chromatography using ether as the eluant and the fractions shown to contain D-6-n-propyl-8α-methoxycarbonylergoline by TLC were combined and the solvent evaporated therefrom. This material moved more slowly on the preparative plate and after separation from a faster moving layer, was combined with fractions 2–6. Evaporation of the solvent from the combined fractions yielded D-6-n-propyl-8α-methoxycarbonylergoline having the following analysis.

Analysis Calculated: C, 73.05; H, 7.74; N, 8.97; Found: C, 72.80; H, 7.81; N, 8.72.
Yield=0.14 g.

EXAMPLE 4

Preparation of
D-6-n-propyl-8α-hydroxymethylergoline

Two grams of an unresolved mixture containing D-6-n-propyl-8β-methoxycrbonylergoline and its 8α-isomer as produced by the procedure of Example 3 were dissolved in 125 ml. of tetrahydrofuran (THF). 2 g. of lithium aluminumhydride were added thereto in portions and the resulting mixture heated to reflux temperature for 1.5 hours. The reaction mixture was then cooled and the excess lithium aluminumhydride decomposed by the addition of ethyl acetate. Ten percent aqueous sodium hydroxide was then added to decompose any organometallics present and the resulting mixture further diluted with water. The alkaline aqueous mixture was extracted several times with a chloroformisopropanol solvent mixture. The organic extracts were combined and the combined extracts washed with saturated aqueous sodium chloride and then dried. Thin layer chromatography of the resulting residue indicated two materials corresponding to D-6-n-propyl-8α-hydroxylmethylergoline and its 8β-isomer. A chloroform solution of the residue was chromatographed over 35 g. of florisil using chloroform containing 2–4 percent methanol as the eluant. Fractions shown to contain identical materials by TLC were combined. 870 mg. of D-6-n-propyl-8β-hydroxymethylergoline melting at 174°–176° C. were obtained by combining fractions shown by TLC to contain this material and then evaporating the solvent therefrom. Other fractions shown by TLC to contain the second component were combined and 110 mg. of D-6-n-propyl-8α-hydroxymethylergoline melting 134°–135° C., after recrystallization from an etherhexane solvent mixture were obtained.

EXAMPLE 5

Preparation of
D-6-n-propyl-8α-mesyloxymethylergoline

About 0.5 g. of D-6-n-propyl-8α-hydroxymethylergoline were dissolved in 20 ml. of pyridine. 0.5 ml. of methanesulfonyl chloride were added and the resulting mixture stirred for about 90 minutes at room temperature. The reaction mixture was then diluted with 10 percent aqueous ammonium hydroxide. The alkaline layer was extracted with ethyl acetate. The ethyl acetate extract was separated, washed with water and with saturated aqueous sodium chloride and then dried. Evaporation of the solvent yielded a residue containing D-6-n-propyl-8α-mesyloxymethylergoline as the major ingredient. A chloroform solution of the residue was chromatographed over 30 g. of florisil using chloroform as the eluant. Fractions shown by TLC to contain D-6-n-propyl-8α-mesyloxymethylergoline were combned and the solvent evaporated from the combined extract. Recrystallization of the resulting residue yielded 500 mg. of D-6-n-propyl-8α-mesyloxymethylergoline melting at about 95° C.

Analysis; Calculated: C, 62.96; H, 7.23; N, 7.73; S, 8.85. Found: C, 62.82; H, 7.24; N, 8.00; S, 8.81.

EXAMPLE 6

Preparation of
D-6-n-propyl-8α-methylmercaptomethylergoline

A solution was prepared from 470 mg. of D-6-n-propyl-8α-mesyloxymethylergoline and 10 ml. of DMF. This solution was added slowly to a solution of the sodium salt of methylmercaptan prepared from 1 ml. of methylmercaptan and 520 mg. of sodium hydride in 25 ml. of DMF. The reaction mixture was stirred at room temperature under a nitrogen atmosphere for 4.5 hours. TLC of an aliquot of the reaction mixture indicated a single spot with a lower $R_f$ value than starting material.

The reaction mixture was diluted with water and the aqueous mixture extracted several times with ethyl acetate. The ethyl acetate extracts were separated and combined and the combined extracts washed with water and then saturated aqueous sodium chloride. The combined extracts were dried and the solvent removed therefrom by evaporation. The resulting residue was dissolved in ether and the ether solution filtered thru florisil. The methanesulfonate salt was prepared by dissolving the residue in 25 ml. of hot methanol. A methanol solution containing an equivalent amount of methanesulfonic acid was added thereto and the solution chilled. The mixture was then diluted with ether and the methanesulfonate salt precipitated. D-6-n-propyl-8α-methylmercaptomethylergoline methane sulfonate melting at 206°–208° C. with decomposition was obtained; yield—200 mg. A second fraction was also obtained; yield=220 mg.

D-6-n-propyl-8α-methoxymethylergoline can be prepared by substituting sodium methylate for the sodium salt of methylmercaptan in the above example.

As evidence of the utility of the compounds of this invention in the treatment of Parkinson's Syndrome, it has been found that they affect turning behavior in a test procedure utilizing 6-hydroxydopamine-lesioned rats. In this test, nigro-neostriatal-lesioned rats are employed, which are prepared by the procedure of Ungerstedt and Arbuthnott, *Brain Res,* 24, 485 (1970). A compound having dopamine agonist activity causes the rats to turn in circles contralateral to the side of the lesion. After a latency period, which varies from compound to compound, the number of turns is counted over a 15-minute period. D-6-n-propyl-8α-methylmercaptomethylergoline mesylate produced an average of 98 turns per lesioned rat at an IP dose of 0.1 mg./kg. and 90 turns at a dose level of 0.05 mg./kg. 100% of the rats exhibited turning at both dosages.

The compounds of this invention are also useful as prolactin inhibitors and as such they can be employed in the treatment of inappropriate lactation such as postpartum lactation and galactorrhea.

As evidence of their utility in the treatment of diseases in which it is desirable to reduce the prolactin level, the compounds of this invention have been shown to inhibit prolactin according to the following procedure.

Adult male rats of the Sprague-Dawley strain weighing about 200 g. were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the ergoline derivative. The purpose of the reserpine was to keep prolactin levels uniformly elevated. D-6-n-propyl-8α-methylmercaptomethylergoline was dissolved in 10 percent ethanol at a concentration of 10 mcg/ml. and injected intraperitoneally at dosages of 5, 50 and 500 mcg/kg. to groups of 10 rats each. A control group of 10 intact males received an equivalent amount of 10 percent ethanol. One hour after treatment all rats were killed by decapitation, and 150 μl aliquots of serum were assayed for prolactin. The results were evaluated statistically using Student's "t" test to calculate the level of significance, "p", of the changes in prolactin level.

The difference between the prolactin level of the treated rats and prolactin level of the control rats, divided by the prolactin level of the control rats gives the percent inhibition of prolactin secretion attributable to the compounds of this invention. These inhibition percentages for D-6-n-propyl-8α-methylmercaptomethylergoline mesylate are given in Table 2 below. In the table, column 1 gives the dose level employed, columns 2 and 3, the serum prolactin levels for the control and treated rats in nanograms/ml; column 4, the percent inhibition, and column 5, the significance level, "p".

TABLE 2

| iP Dose mcg/kg | Serum Prolactin (ng/ml) | | % Inhibition of Serum Prolactin | Significance Level "P" |
|---|---|---|---|---|
| | Control | Treated | | |
| 500 | 17.7 ± 2.6 | 1.9 ± 0.5 | 89% | P<0.001 |
| 50 | 17.7 ± 2.6 | 1.6 ± 0.3 | 91% | P<0.001 |
| 5 | 17.7 ± 2.6 | 4.6 ± 0.7 | 74% | P<0.001 |

The compounds of this invention also reduce blood pressure in spontaneously hypertensive rats and are therefore potentially useful in the treatment of hypertension in mammals.

In using the compounds of this invention to inhibit prolactin secretion or to treat Parkinson's syndrome or for other pharmacologic action, an ergoline, according to Formula II above, or a salt thereof with a pharmaceutically-acceptable acid, is administered to a subject suffering from Parkinsonism, or in need of having their prolactin level reduced, in amounts ranging from 0.01 to 3 mg per kg. of mammalian weight. For D-6-n-propyl-8α-methylmercaptomethylergoline, a dose range of 0.01 to 0.5 mg/kg. is used. Oral administration is preferred. If parenteral administration is used, the injection is preferably by the subcutaneous route using an appropriate pharmaceutical formulation. Other modes of parenteral administration such as intraperitoneal, intramuscular, or intravenous routes are equally effective. In particular, with intravenous or intramuscular administration, a water soluble pharmaceutically-acceptable salt is employed. For oral administration, a compound according to Formula II either as the free base or in the form of a salt thereof can also be mixed with standard pharmaceutical excipients and loaded into empty telescoping gelatin capsules or pressed into tablets.

What is claimed is:

1. A process for treating a patient suffering from Parkinson's syndrome and in need of treatment which comprises adminstering a dose, effective to ameliorate the Parkinsonism symptoms, of a compound of the formula

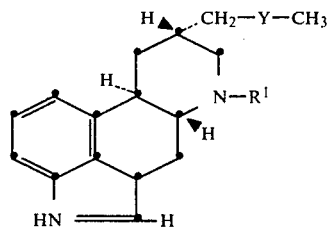

wherein Y is O, or S and R¹ is n-propyl, and pharmaceutically-acceptable acid addition salts thereof.

2. A process for inhibiting the secretion of prolactin in mammals which comprises administering to a mammal in which there is an excess of prolactin being secreted a prolactin-lowering dose of a compound of the formula

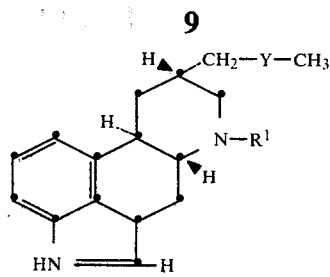

wherein Y is O, or S and R[1] is n-propyl, and pharmaceutically-acceptable acid addition salts thereof.

3. A method according to claim 1 in which D-6-n-propyl-8α-methylmercaptomethylergoline or a pharmaceutically acceptable salt thereof is administered.

4. A process according to claim 2 in which D-6-n-propyl-8α-methylmercaptomethylergoline or a pharmaceutically-acceptable salt thereof is administered.

* * * * *